United States Patent [19]

Casas et al.

[11] Patent Number: 5,534,253

[45] Date of Patent: Jul. 9, 1996

[54] METHOD OF TREATING ENTEROPATHOGENIC BACTERIAL INFECTIONS IN POULTRY

[75] Inventors: Ivan A. Casas, Raleigh, N.C.; Bo Mollstam, Lerum, Sweden

[73] Assignee: Biogaia AB, Stockholm, Sweden

[21] Appl. No.: 474,101

[22] Filed: Jun. 7, 1995

[51] Int. Cl.$^6$ ..................................................... A01N 63/00
[52] U.S. Cl. ........................................... 424/93.45; 514/39
[58] Field of Search ...................... 424/93.45; 514/35–41

[56] References Cited

U.S. PATENT DOCUMENTS

| | | | |
|---|---|---|---|
| 3,984,575 | 10/1976 | Farr | 426/61 |
| 4,048,299 | 9/1977 | Litchfield | 424/49 |
| 4,335,107 | 6/1982 | Snoeyenbos | 424/93.3 |
| 4,518,696 | 5/1985 | Gehrman | 435/252.9 |
| 4,689,226 | 8/1987 | Nurmi | 424/93.3 |
| 4,710,379 | 12/1987 | Kawai | 424/93.44 |

FOREIGN PATENT DOCUMENTS

| | | |
|---|---|---|
| 190707 | 9/1985 | Japan . |
| 275217 | 12/1986 | Japan . |

OTHER PUBLICATIONS

Axelsson, L. et al., "Characterization and DNA Homology of Lactobacillus Strains Isolated from Pig Intestine", J. Appl. Bacteriol. 62:433–440, 1987.

Axelsson, L et al., "Production of a Broad Spectrum Antimicrobial Substance by *Lactobacillus reuteri*", Microbial Ecology in Health and Disease 2:131–136, 1989.

Chung, T C et al., "In vitro Studies on Reuterin Synthesis by *Lactobacillus reuteri*", Microbial Ecology in Health and Disease 2:137–144, 1989.

Daeschel, M A, "Antimicrobial Substances from Lactic Acid Bacteria for Use as Food Preservatives", Food Tech. 43: 164–167, 1989.

Dobrogosz, W J et al., "Delivery of Viable *Lactobacillus reuteri* to the Gastrointestinal Tract of Poultry", research report presented at Southern Poultry Science Society Meeting, Jan. 28–29, 1991, Atlanta, Georgia.

Dobrogosz, W J et al., "*Lactobacillus reuteri* and the Enteric Microbiota", in *Regulatory and Protective Role of the Normal Microflora*, from the Gustafsen Symposium, McMillan Ltd, 1989, pp. 283–292.

Edens, F W et al., "*Lactobacillus reuteri* and Whey Reduce Salmonella Colonization in the Ceca of Turkey Poults", research report presented at Southern Poultry Science Society Meeting, Jan. 28–29, 1991, Atlanta, Georgia.

Francis, C et al., "Interrelationship of Lactobacillus and Zinc Bacitracin in the Diets of Turkey Poults", Poultry Sci. 57:1687–1689, 1978.

Fuller, R, "Probiotics", J. Appl. Bacteriol. Symp. Supp. 1986, IS–7S.

Gerhardt, P et al., *Manual of Methods for General Bacteriology*, 1981, p. 120.

Kandler, O et al., "Regular, Nonsporing Gram–Positive Rods", in Sneath, P H A et al., *Bergey's Manual of Systematic Bacteriology*, vol. 2, 1986, Williams & Wilkins.

Klaenhammer, T R, "Microbiological Considerations in Selection and Preparation of Lactobacillus Strains for Use as Dietary Adjuncts", Dairy Sci. 65:1339–1349, 1982.

Parkhurst, C R et al., "*Lactobacillus reuteri* and Dietary Whey Effect on Twenty Day Body Weights of Turkey Poults Subjected to Either Cold or Low Protein Stress", research report presented at Southern Poultry Science Society Meeting, Jan. 28–29, 1991, Atlanta, Georgia.

Snoeyenbos, G H et al., "Protecting Chicks and Poults from Salmonellae by Oral Administration of Normal Gut Microflora", Avian Dis. 22:273–287, 1978.

Talarico, T L et al., "Chemical Characterization of an Antimicrobial Substance Produced by *Lactobacillus reuteri*", Antimicrobial Agents and Chemotherapy 33:674–679, 1989.

*Primary Examiner*—Michael G. Wityshyn
*Assistant Examiner*—Jean C. Witz
*Attorney, Agent, or Firm*—Olive & Olive

[57] ABSTRACT

A method of improving animal health including selecting at least one *L. reuteri* strain, characterized by the production of β-hydroxypropionaldehyde, and using the selected strain(s) along with the antibiotic, gentamycin, as an animal treatment, for example, for newly hatched poultry.

6 Claims, 1 Drawing Sheet

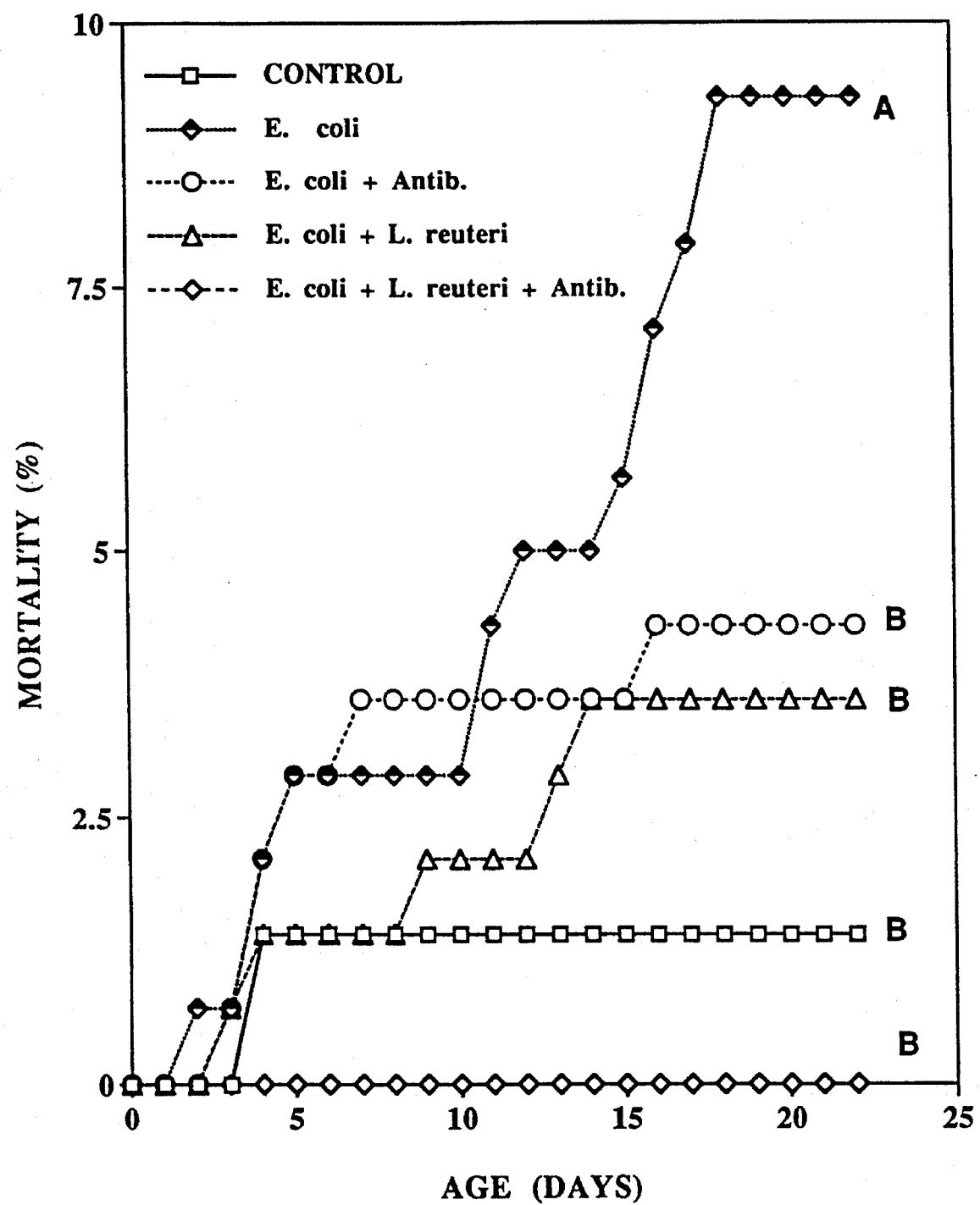

METHOD OF TREATING ENTEROPATHOGENIC BACTERIAL INFECTIONS IN POULTRY

BACKGROUND OF THE INVENTION

1. Field of the Invention

This invention relates to methods utilizing synergistic effects between antibiotics and probiotics for improving animal health.

2. Description of the Related Art

Microbial contamination of animals which are very susceptible to microbial pathogens often leads to disease and increased animal morbidity. In commercial animal growing operations where animals may be crowded in facilities where other animals have been previously raised, the likelihood of such contamination is often great. This is particularly true in the poultry industry. Early chick mortality (ECM) is often associated with microbial exposure during incubation, hatching and processing. Pathogenic microorganisms often reside on and within the egg shell, and there is wide dissemination of egg-borne pathogens at hatching. Researchers over the years have tested numerous antimicrobial substances to see if they would improve animal mortality.

Numerous probiotic species have also been tested for efficacy in improving animal health. Many of these tests have utilized various species of the *Lactobacillaceae*, such as species of *Lactobacillus* and *Streptococcus*. Most of these tests have shown limited utility and practicability at best.

Work by Dobrogosz and Lindgren, and their collaborators in the mid-1980's, which has been the subject of a number of publications, however, showed that *Lactobacillus reuteri* strains are unique in producing an antibiotic substance identified as β-hydroxypropionaldehyde. (See for example, Dobrogosz, WJ, Casas IA, Pagano, GA, Talarico, TL, Sjoberg, B, and M Karlsson, *Lactobacillus reuteri* and the Enteric Microbiota, in *Regulatory and Protective Role of the Normal Microflora*, from the Gustafsen Symposium, McMillan Ltd, 1989, pages 283–292; and Dobrogosz, WJ and SE Lindgren, Antibiotic Reuterin, International Application Published under the Patent Cooperation Treaty (PCT), PCT/US88/01423, published November 3, 1988).

Further, *L. reuteri* was shown to be effective in inhibiting *Salmonella*, in increasing gastrointestinal villi growth, in increasing animal weight gain, and in improving mortality. In ovo and spraying techniques have been shown to be useful in delivering *Lactobacillus reuteri* cells to poultry to reduce ECM, as an alternative to traditional antibiotic usage.

While various previous treatments have resulted in improved mortality, there has continued a real need to reduce the number of animal deaths even further.

It is therefore an object of this invention to provide a method of improving animal health, particularly mortality of poultry, such as chickens and turkeys.

Other objects and advantages will be more fully apparent from the following disclosure and appended claims.

SUMMARY OF THE INVENTION

The method of the invention for improving animal health, for example, for newly hatched poultry, includes the steps of selecting at least one *L. reuteri* strains, characterized by the production of β-hydroxypropionaldehyde, and using the selected strain(s) along with the antibiotic, gentamycin, as a treatment.

Other aspects and features of the invention will be more fully apparent from the following disclosure and appended claims.

BRIEF DESCRIPTION OF THE DRAWINGS

The FIGURE is a graph showing broiler mortality over time for the five treatments discussed in Example I. Treatment (1) is shown by open squares, treatment (2) is shown by half closed diamonds, treatment (3) is shown by open circles, treatment (4) is shown by open triangles, and treatment 5 is shown by open diamonds.

DETAILED DESCRIPTION OF THE INVENTION AND PREFERRED EMBODIMENTS THEREOF

The present invention is a method of improving animal health, comprising:

(a) selecting a strain of *Lactobacillus reuteri*, which is characterized as producing β-hydroxypropionaldehyde under anaerobic conditions in the presence of glycerol or glyceraldehyde;

(b) administering cells of said strain to said animals; and (c) treating said animals with gentamycin.

In the preferred embodiments, the cells are administered by spraying the animals daily, and/or by feeding the animals a feed containing *L. reuteri*. In addition, *L. reuteri* administration may comprise egg injection prior to hatch, or spraying of the eggs prior to hatch. The invention herein shows the synergistic effect of establishing *L. reuteri* in the animal in an amount sufficient to colonize the gastrointestinal tract of said animal, and treating the animal with gentamycin.

For a particular animal system, *Lactobacillus reuteri* capable of colonizing the animals' gastointestinal tract can be obtained from culture collections or from natural isolates from healthy animals. Methods for such isolation are explained in detail in the above-cited PCT application of Dobrogosz et al. If the amount of *Lactobacillus reuteri* inoculum for the particular animal system and type of treatment is not known for that system, preliminary routine experimentation to determine the amount sufficient to result in colonization can be performed, using the overlay method reported in the PCT application of Dobrogosz et al. to determine presence and number of *Lactobacillus reuteri*. Typically, an amount of $10^3$–$10^4$ per animal, administered at one time, or over multiple days, is found to be sufficient to colonize the animal's gastrointestinal tract. The use of additional *L. reuteri* cells, as in the example herein, provides added assurance of substantial, rapid colonization. Similarly, using more than one type of *L. reuteri* treatment optimizes the colonization as does early treatment in the life of the animal.

The features and advantages of the present invention will be more clearly understood by reference to the following example, which is not to be construed as limiting the invention.

EXAMPLE I

Treatment with *L. reuteri* and *Gentamycin*

Eggs which have been incubated for 18 days are placed in two hatcher consoles. The eggs in one console are sprayed with water 24 hours before the eggs are to hatch, and the eggs in the other console are sprayed with *Lactobacillus*

*reuteri* cells 24 hours before hatching. In the experiment for which results are given below, 0.1 ml/egg was sprayed, at a level of $10^7$ cells per ml. The *L. reuteri* strain(s) used may be any strain that colonizes the animals to be treated, which in the example below, are chickens. The strain of *L. reuteri* used in the example is strain number 11284, ATCC No. 55148, deposited under the Budapest Treaty with the American Type Culture Collection, Rockville, Md., on Jan. 29, 1991.

Immediately after hatch, the five treatments are as follows:

(1) absolute control—no *L. reuteri* added, no enteropathogenic *E. coli*, no gentamycin (30 birds hatched from previously water sprayed eggs);

(2) *E. coli* control—$10^4$ CFU enteropathogenic *E. coli* are gavaged into each of 30 birds hatched from eggs which were previously water sprayed;

(3) *E. coli* plus gentamycin—*E. coli* as in treatment (2) plus 0.2 mg gentamycin sulfate administered by subcutaneous injection using standard techniques into each of 30 birds hatched from eggs which were previously water sprayed;

(4) *E. coli* plus *L. reuteri*—*E. coli* as in treatment (2) with 30 birds from eggs sprayed with *L. reuteri* prior to hatch, plus feeding with GAIAfeed™, containing about $10^5$ CFU per gram *L. reuteri*, as 2% of the hatched birds' feed for eleven days post hatch; and (5) *E. coli* and *L. reuteri* as in treatment (4), and gentamycin sulfate as in treatment (3) with 30 birds hatched from eggs sprayed with *L. reuteri* prior to hatch.

After the treatment above, chicks are transferred to Petersime brooders. Each treatment is placed into a separate but identically controlled isolation room. Mortality is determined daily, and body weights are determined at 21 days. Cecal *E. coli* and *L. reuteri* are determined at hatch and at the end of the experiment to assure that there was no cross-contamination.

Typical results of mortality and body weights at day 22 are shown in Table 1.

TABLE 1

| TREATMENT | BODY WEIGHT (g)* | MORTALITY (%)* |
|---|---|---|
| (1) Absolute control | 842b | 1.42b |
| (2) *E. coli* only | 803b | 9.52a |
| (3) *E. coli* + gentamycin | 819b | 4.26b |
| (4) *E. coli* + *L. reuteri* | 874a | 3.56b |
| (5) *E. coli* + *L. reuteri* + gentamycin | 882a | 0.00b | a,b In a column, means if unlike, are different ($P \leq .01$)
*at 22 days of age Mortality results from day 0 to day 25 are shown in FIG. 1 and show the differences between treatments over time.

The results of this experiment show that spraying of eggs with *L. reuteri* and addition of *L. reuteri* to the feed, in combination with gentamycin sulfate treatment, provides excellent protection against *E. coli*-associated mortality. Body weight is increased significantly over use of gentamycin alone, and mortality is essentially eliminated.

Further experimentation shows that similar results are obtained when eggs are injected with *L. reuteri* in addition to or instead of spraying of the eggs. Optimal results are obtained as the establishment of *L. reuteri* is maximized in conjunction with the gentamycin sulfate treatment.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention. Particularly also included within the invention is the use of *L. reuteri* treatment as is known in the art on any young animal, along with treatment with an antibiotic.

What is claimed is:

1. A method of treating enteropat/Logenic bacterial infections in poultry, comprising:

(a) selecting a strain of *Lactobacillus reuteri*, which is characterized as producing β-hydroxypropionaldehyde under anaerobic conditions in the presence of glycerol or glyceraldehyde;

(b) administering an effective amount of cells of said strain to said poultry; and (c) treating said poultry with an effective amount of gentamycin.

2. The method according to claim 1, wherein said administering comprises spraying said poultry with said cells in an amount sufficient to colonize the gastrointestinal tract of said poultry.

3. The method according to claim 1, wherein said administering comprises feeding said poultry a feed containing *Lactobacillus reuteri* cells.

4. The method according to claim 3, wherein the feed contains about $10^5$ CFU *Lactobacillus reuteri* per gram feed.

5. The method according to claim 2, wherein said administering further comprises feeding said poultry a feed containing *Lactobacillus reuteri* cells.

6. The method according to claim 5, wherein the feed contains about $10^5$ CFU *Lactobacillus reuteri* per gram feed.

\* \* \* \* \*

UNITED STATES PATENT AND TRADEMARK OFFICE
CERTIFICATE OF CORRECTION

PATENT NO. : 5,534,253
DATED : July 9, 1996
INVENTOR(S) : Ivan A. Casas and Bo Mollstam It is certified that error appears in the above-identified patent and that said Letters Patent is hereby corrected as shown below:

Column 4, line 26, replace "enteropat/Logenic" with --enteropathogenic--.

Signed and Sealed this

Twenty-sixth Day of August, 1997

Attest:

BRUCE LEHMAN

*Attesting Officer*   *Commissioner of Patents and Trademarks*